(12) United States Patent
Kawahara

(10) Patent No.: US 11,986,154 B2
(45) Date of Patent: May 21, 2024

(54) OPTICAL TRANSDUCER FOR ENDOSCOPE, ENDOSCOPE, AND MANUFACTURING METHOD OF OPTICAL TRANSDUCER FOR ENDOSCOPE

(71) Applicant: OLYMPUS CORPORATION, Tokyo (JP)

(72) Inventor: Kosuke Kawahara, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 560 days.

(21) Appl. No.: 17/225,295

(22) Filed: Apr. 8, 2021

(65) Prior Publication Data

US 2021/0251471 A1 Aug. 19, 2021

Related U.S. Application Data

(63) Continuation of application No. PCT/JP2018/038500, filed on Oct. 16, 2018.

(51) Int. Cl.
*A61B 1/00* (2006.01)
*A61B 1/05* (2006.01)
*G02B 6/42* (2006.01)
*G02B 23/26* (2006.01)

(52) U.S. Cl.
CPC ........ *A61B 1/0017* (2013.01); *A61B 1/00013* (2013.01); *A61B 1/05* (2013.01); *G02B 6/424* (2013.01); *G02B 23/26* (2013.01)

(58) Field of Classification Search
CPC ........... A61B 1/0013; A61B 1/05; A61B 1/07; A61B 1/0684; G02B 6/424; G02B 6/4212; G02B 6/4292; G02B 23/26; H01L 33/58
See application file for complete search history.

(56) References Cited

U.S. PATENT DOCUMENTS

2016/0266341 A1\* 9/2016 Park .................. G02B 6/4295
2017/0082806 A1 3/2017 Van Der Mark et al.
2018/0078114 A1 3/2018 Kobayashi

FOREIGN PATENT DOCUMENTS

JP 2001-290052 A 10/2001
JP 2002-228882 A 8/2002
JP 2004-004333 A 1/2004

(Continued)

OTHER PUBLICATIONS

International Search Report dated Dec. 18, 2018 issued in PCT/JP2018/038500.

*Primary Examiner* — Timothy J Neal
(74) *Attorney, Agent, or Firm* — Scully, Scott, Murphy & Presser, P.C.

(57) ABSTRACT

An optical transducer for endoscope includes an optical device, a ferrule including an opaque first holding member including a first principal surface, a second principal surface, and a through-hole, and a transparent second holding member including a third principal surface and a fourth principal surface, the third principal surface of the second holding member abutting on the second principal surface, the optical device being bonded to the fourth principal surface, the third principal surface including a recess including an opening and having a bottom, the recess having the bottom communicating with the through-hole, and an optical fiber provided in the recess through the through-hole.

19 Claims, 8 Drawing Sheets

(56) References Cited

FOREIGN PATENT DOCUMENTS

| | | | | |
|---|---|---|---|---|
| JP | 2015087744 A | * | 5/2015 | ......... A61B 1/00013 |
| JP | 2015097588 A | * | 5/2015 | ......... A61B 1/00013 |
| JP | 2017-516128 A | | 6/2017 | |
| WO | 2015/150149 A1 | | 10/2015 | |
| WO | 2016/189691 A1 | | 12/2016 | |
| WO | 2018/037551 A1 | | 3/2018 | |
| WO | 2018/150512 A1 | | 8/2018 | |

* cited by examiner

OPTICAL TRANSDUCER FOR ENDOSCOPE, ENDOSCOPE, AND MANUFACTURING METHOD OF OPTICAL TRANSDUCER FOR ENDOSCOPE

CROSS REFERENCE TO RELATED APPLICATION

This application is a continuation application of PCT/JP2018/038500 filed on Oct. 16, 2018, the entire contents of which are incorporated herein by this reference.

BACKGROUND OF THE INVENTION

1. Field of the Invention

The present invention relates to an optical transducer for endoscope which includes an optical device, an optical fiber and a ferrule, an endoscope including the optical transducer for endoscope which includes the optical device, the optical fiber and the ferrule, and a manufacturing method of the optical transducer for endoscope which includes the optical device, the optical fiber and the ferrule.

2. Description of the Related Art

An endoscope includes an image pickup device at a distal end portion of an elongated insertion portion. An image pickup device having a large number of pixels has been studied to display a high-quality image. Use of an image pickup device having a large number of pixels increases a signal amount to be transmitted from the image pickup device to a signal processing apparatus (processor).

Optical signal transmission in which an optical signal in place of an electrical signal is transmitted by way of a thin optical fiber is preferable to make the insertion portion thinner and achieve a less-invasive endoscope. The optical signal transmission uses an E/O type optical transducer (electrical-to-optical converter) including a light emitting element which converts an electrical signal into an optical signal, and an O/E type optical transducer (optical-to-electrical converter) including a light receiving element which converts an optical signal into an electrical signal. The optical fiber is inserted into an insertion hole of a ferrule of the optical transducer and fixed.

The optical transducer disposed at the distal end portion of the insertion portion of the endoscope is ultracompact to achieve a less-invasive endoscope.

FIG. 8 of International Publication No. 2018/037551 discloses a ferrule made of a transparent member.

SUMMARY OF THE INVENTION

An optical transducer for endoscope of an embodiment includes an optical device including a light emitting surface from which an optical signal is outputted, a bonded electrode being disposed on the light emitting surface, a ferrule including an opaque first holding member including a first principal surface, a second principal surface on an opposite side of the first principal surface, and a through-hole, and a transparent second holding member including a third principal surface and a fourth principal surface on an opposite side of the third principal surface, the third principal surface of the second holding member abutting on the second principal surface, the fourth principal surface including a wiring, the bonded electrode of the optical device being bonded to the wiring, the third principal surface including a recess including an opening and having a bottom, the recess having the bottom communicating with the through-hole, and an optical fiber provided in the recess through the through-hole and configured to transmit the optical signal.

An optical transducer for endoscope of an embodiment includes an optical device configured to generate an optical signal, a ferrule including a first holding member made of silicon and including a first principal surface, a second principal surface facing the first principal surface, and a through-hole, and a second holding member made of glass and including a third principal surface and a fourth principal surface facing the third principal surface, the third principal surface abutting on the second principal surface, the optical device being mounted on the fourth principal surface, the third principal surface including a recess including an opening and having a bottom, the recess having the bottom communicating with the through-hole, and an optical fiber provided in the recess through the through-hole and configured to transmit the optical signal.

An endoscope of an embodiment includes an optical transducer for endoscope, the optical transducer for endoscope including an optical device including a light emitting surface from which an optical signal is outputted, a bonded electrode being disposed on the light emitting surface, a ferrule including an opaque first holding member including a first principal surface, a second principal surface on an opposite side of the first principal surface, and a through-hole, and a transparent second holding member including a third principal surface and a fourth principal surface on an opposite side of the third principal surface, the third principal surface of the second holding member abutting on the second principal surface, the fourth principal surface including a wiring, the bonded electrode of the optical device being bonded to the wiring, the third principal surface including a recess including an opening and having a bottom, the recess having the bottom communicating with the through-hole, and an optical fiber provided in the recess through the through-hole and configured to transmit the optical signal.

An endoscope of an embodiment includes an optical transducer for endoscope, the optical transducer for endoscope including an optical device configured to generate an optical signal, a ferrule including a first holding member made of silicon and including a first principal surface, a second principal surface facing the first principal surface, and a through-hole, and a second holding member made of glass and including a third principal surface and a fourth principal surface facing the third principal surface, the third principal surface abutting on the second principal surface, the optical device being mounted on the fourth principal surface, the third principal surface including a recess including an opening and having a bottom, the recess having the bottom communicating with the through-hole, and an optical fiber provided in the recess through the through-hole and configured to transmit the optical signal.

A manufacturing method of an optical transducer for endoscope of an embodiment includes preparing an opaque first substrate including a first principal surface and a second principal surface on an opposite side of the first principal surface, the second principal surface including a protrusion, preparing a bonded substrate by disposing a transparent second substrate on the second principal surface and embedding the protrusion into the second substrate, forming, through an etching process, a through-hole and a recess on the bonded substrate, the through-hole being inscribed in space located in an extension of the protrusion in an optical axis direction, the recess communicating with the through-hole and having a same inside dimension as an inside dimension of the through-hole, and inserting an optical fiber into the recess through the through-hole.

DETAILED DESCRIPTION OF THE PREFERRED EMBODIMENTS

<Endoscope>

Figure 1:
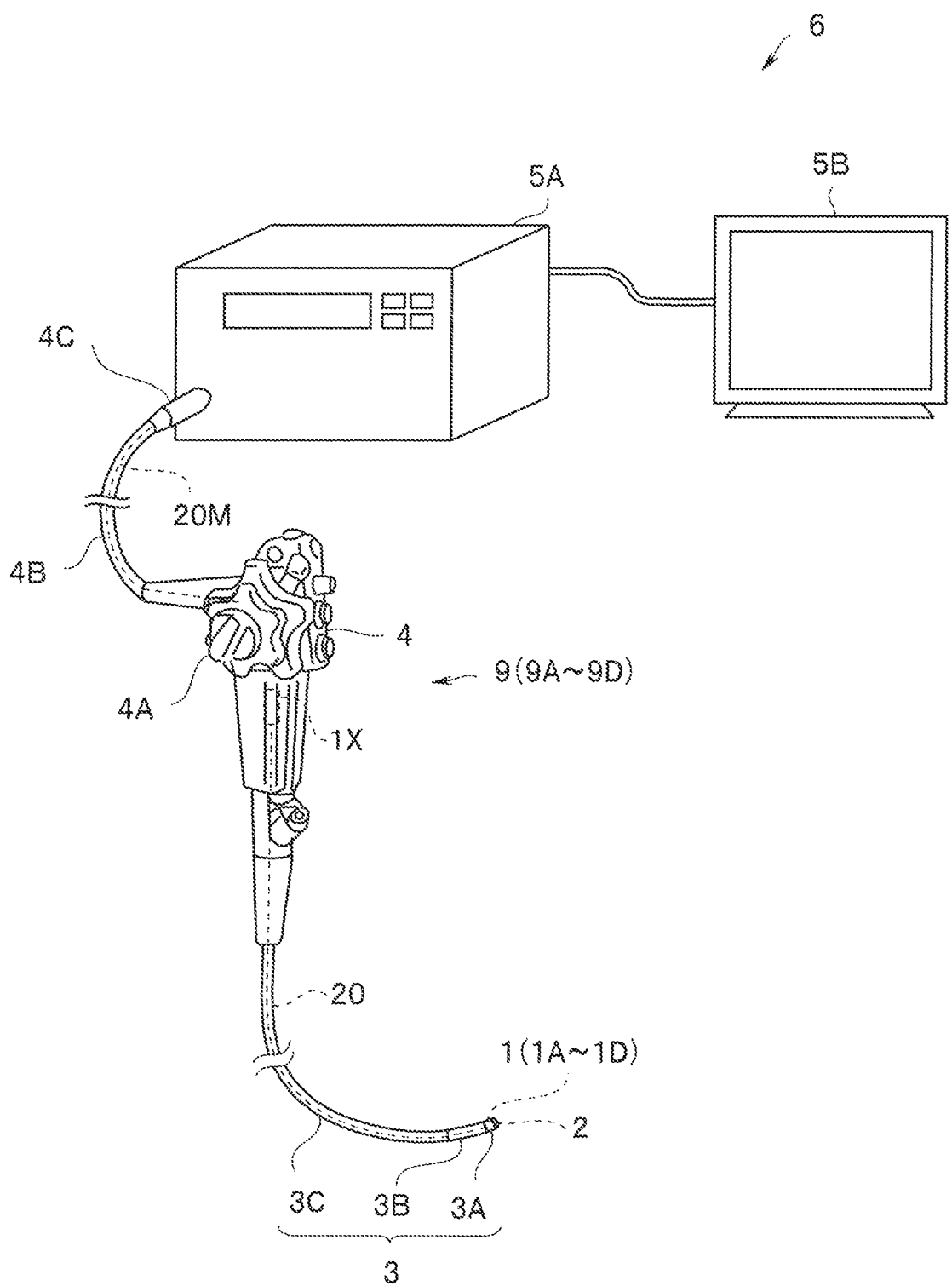
FIG. 1 is a perspective view of an endoscope system including an endoscope of an embodiment.

As illustrated in FIG. 1, an endoscope 9 of an embodiment constitutes an endoscope system 6 with a processor 5A and a monitor 5B. The endoscope 9 includes an optical transducer for endoscope 1 (hereinafter, referred to as an "optical transducer 1") of the embodiment.

The endoscope 9 includes an insertion portion 3, a grasping portion 4 disposed at a proximal end portion of the insertion portion 3, a universal cord 4B extended from the grasping portion 4, and a connector 4C disposed at a proximal end portion of the universal cord 4B. The insertion portion 3 includes a distal end portion 3A, a bending portion 3B which is extended from the distal end portion 3A, which can be freely bent, and which is provided for changing a direction of the distal end portion 3A, and a flexible portion 3C extended from the bending portion 3B. The optical transducer 1 and an image pickup device 2 are disposed at the distal end portion 3A. A rotary angle knob 4A which is an operation portion to be used by an operator to operate the bending portion 3B is disposed at the grasping portion 4.

The universal cord 4B is connected to the processor 5A with the connector 4C. The processor 5A controls the whole endoscope system 6, performs signal processing on an image pickup signal and outputs the signal subjected to the signal processing as an image signal. The monitor 5B displays the image signal outputted by the processor 5A as an endoscope image. Note that while the endoscope 9 is a flexible endoscope, the endoscope 9 may be a rigid endoscope. Further, the endoscope 9 may be an endoscope for medical use or an endoscope for industrial use.

The image pickup device 2 and the optical transducer 1 are disposed at the distal end portion 3A of the endoscope 9. The optical transducer 1 is an E/O type optical transducer which converts an electrical signal outputted by the image pickup device 2 into an optical signal. The image pickup device 2 is a CMOS image sensor, a CCD, or the like.

The optical signal is converted into an electrical signal again by an O/E type optical transducer 1X disposed at the grasping portion 4, by way of an optical fiber 20 which passes through the insertion portion 3 and transmitted by way of a metal wiring 20M. In other words, the image pickup signal is transmitted by way of the optical fiber 20 at the thin insertion portion 3 and transmitted by way of a signal cable which is the metal wiring 20M thicker than the optical fiber 20 within the universal cord 4B which is not inserted inside the body and which has less restriction on an outer diameter.

Note that in a case where the O/E type optical transducer 1X is disposed at the connector 4C, the optical fiber 20 passes through the universal cord 4B.

While the optical transducer 1X is disposed at the grasping portion 4 which has relatively large space for arrangement, the optical transducer 1X may have the same configuration as the configuration of the optical transducer 1. Further, the optical transducer 1 disposed at the grasping portion 4 may convert a control signal to the image pickup device 2 into an optical signal, and the optical transducer 1X disposed at the distal end portion 3A may convert the optical signal into an electrical signal.

As will be described later, the optical transducer 1 has high reliability and high transmission efficiency. Thus, the endoscope 9 including the optical transducer 1 displays an image with high reliability and with high quality.

First Embodiment

Figure 2:
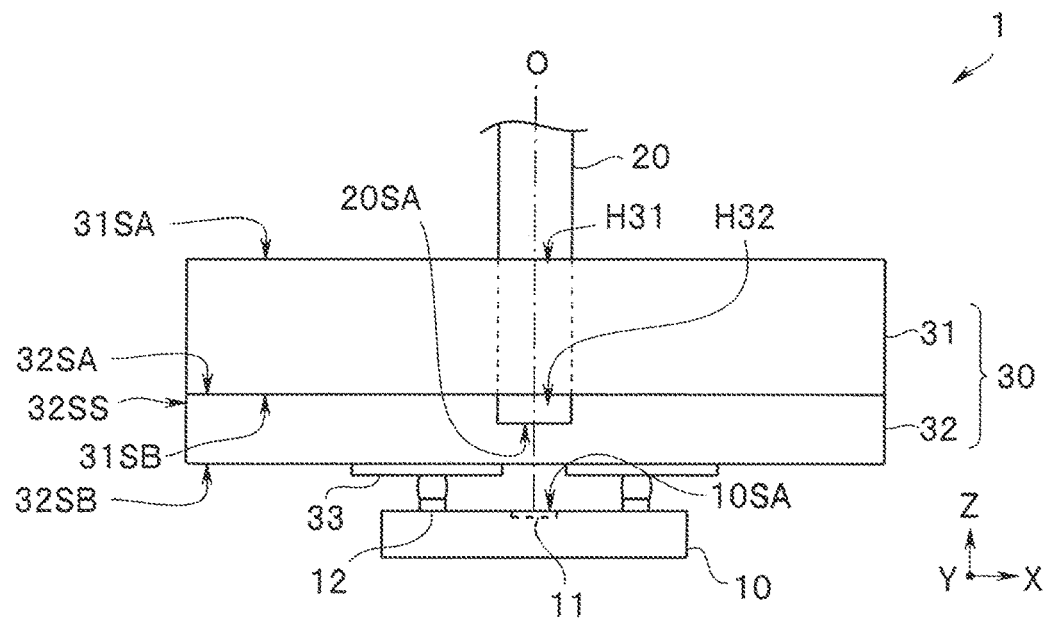
FIG. 2 is a side view of an optical transducer of a first embodiment.
Figure 3:
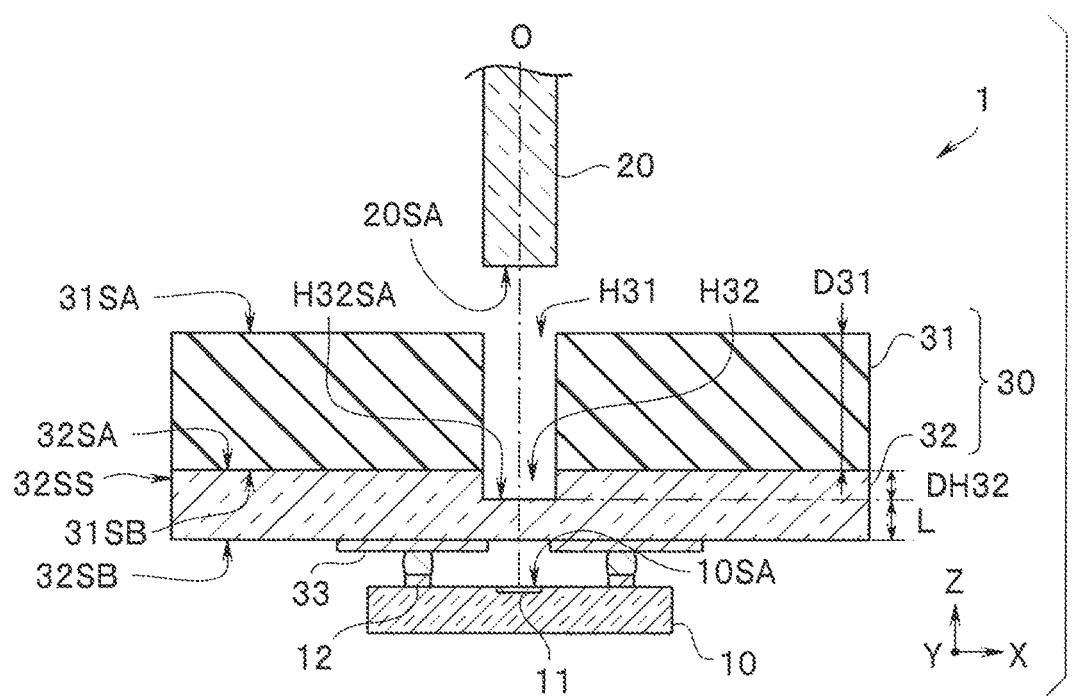
FIG. 3 is an exploded cross-sectional view of the optical transducer of the first embodiment.

As illustrated in FIG. 2 and FIG. 3, the optical transducer 1 of the present embodiment includes an optical device 10 which is a light emitting element, an optical fiber 20, and a ferrule 30.

Note that in the following description, drawings based on respective embodiments are schematically illustrated, and relationship between a thickness and a width of each portion, a ratio of a thickness of each portion, and the like, are different from real relationship, a real ratio, and the like. The drawings may include portions in which relationship and a ratio of dimensions differ between the drawings. Further, illustration and reference numerals of part of components may be omitted.

The optical device 10 includes a light emitting surface 10SA from which an optical signal is outputted, and a plurality of bonded electrodes 12 are disposed on the light emitting surface 10SA. For example, an ultracompact optical device 10 having a planar dimension of 250 μm×250 μm is a VCSEL (vertical cavity surface emitting laser) or a light emitting diode including a light emitting region 11 with a diameter of 10 μm, and a plurality of bonded electrodes 12 which supply drive signals to the light emitting region 11, on the light emitting surface 10SA.

The image pickup signal outputted by the image pickup device 2 is converted into a drive signal which drives the optical device 10 by a drive circuit (not illustrated) and inputted to the bonded electrodes 12.

The optical fiber 20 which transmits an optical signal includes, for example, a core having a radius of 50 μm which transmits the optical signal, and a clad having a radius of 125 μm which covers an outer circumference of the core.

The ferrule 30 includes a first holding member 31 and a second holding member 32. The first holding member 31 includes a first principal surface 31SA and a second principal surface 31SB on an opposite side of the first principal surface 31SA. The second holding member 32 includes a third principal surface 32SA and a fourth principal surface 32SB on an opposite side of the third principal surface 32SA. The third principal surface 32SA of the second holding member 32 abuts on the second principal surface 31SB of the first holding member 31.

The optical device 10 is mounted on the fourth principal surface 32SB of the second holding member 32. In other words, the bonded electrodes 12 of the optical device 10 are bonded to a wiring 33 of the second holding member 32.

The first holding member 31 is made of silicon which is an opaque member. The second holding member 32 is made of glass which is a transparent member. The opaque member and the transparent member may be made of, for example, a resin.

A through-hole H31 is provided at the first holding member 31. The second holding member 32 includes a recess H32 including an opening on the third principal surface 32SA and having a bottom. The recess H32 having the bottom communicates with the through-hole H31.

A tip end of the optical fiber 20 is inserted into the recess H32 through the through-hole H31. Space A (three-dimensional range A) (see FIG. 7) from four side surfaces 32SS of the second holding member 32 to the distal end of the optical fiber 20 is formed of glass which is a transparent member. It is therefore possible to confirm a position of a distal end surface 20SA of the optical fiber 20 from the side surfaces of the second holding member 32.

Note that the distal end surface 20SA of the optical fiber 20 abuts on a bottom H32SA of the recess H32 in the optical transducer 1. However, even if there is a gap between the distal end surface 20SA of the optical fiber 20 and the bottom H32SA of the recess H32, if a length of the gap is equal to or less than a predetermined length, optical transmission efficiency does not particularly largely decrease. In other words, it is only necessary that the distal end surface of the optical fiber is located between the bottom H32SA of the recess H32 and the third principal surface 32SA.

For example, the through-hole H31 and the recess H32 both have cross-sections orthogonal to an optical axis O in the shape of a circle having a radius of 130 μm and have wall surfaces perpendicular to the principal surfaces, and thus, an inside dimension (inner diameter) of the through-hole H31 and an inside dimension (inner diameter) of the recess H32 do not change in a depth direction.

A depth of the through-hole H31, that is, a thickness D31 of the first holding member 31 is preferably equal to or greater than 50 μm to stably hold the optical fiber 20. A distance L from the bottom H32SA of the recess H32 to the fourth principal surface 32SB is, for example, equal to or greater than 10 μm and equal to or less than 100 μm. If the distance L is equal to or greater than the above-described range, the second holding member 32 is less likely to be broken when the optical fiber 20 is inserted, and if the distance L is equal to or less than the above-described range, favorable transmission efficiency of optical signals can be obtained. Further, a distance from the third principal surface 32SA to the bottom H32SA of the recess H32, that is, a lower limit of a depth DH32 of the recess H32 is preferably, for example, equal to or greater than 10 μm so as to allow the distal end surface 20SA to be visually confirmed from the side surface. An upper limit of the depth DH32 is preferably, for example, equal to or less than 50 μm to make it easier to form the recess H32 and to prevent the second holding member 32 from being broken.

The optical transducer 1 allows confirmation of a distance between the distal end surface 20SA of the optical fiber 20 and the light emitting region 11 of the optical device 10, so that, there is no possibility that transmission efficiency of optical signals may decrease.

It goes without saying that the position of the distal end surface 20SA may be observed using a monitor screen of a microscope as well as being visually confirmed.

A transparent resin having a refractive index matching function which prevents interface reflection may be interposed between the distal end surface 20SA of the optical fiber 20 and the bottom H32SA of the recess H32.

The transparent resin which covers the distal end surface 20SA of the optical fiber 20 also covers an outer circumference near the distal end surface 20SA. Thus, the space A from the side surface 32SS of the second holding member 32 to the distal end of the optical fiber 20 is formed of a transparent member (glass and a transparent resin). It is therefore possible to visually confirm the position of the distal end surface 20SA of the optical fiber 20 from the side surface of the second holding member 32.

<Manufacturing Method of Optical Transducer>

Figure 4:
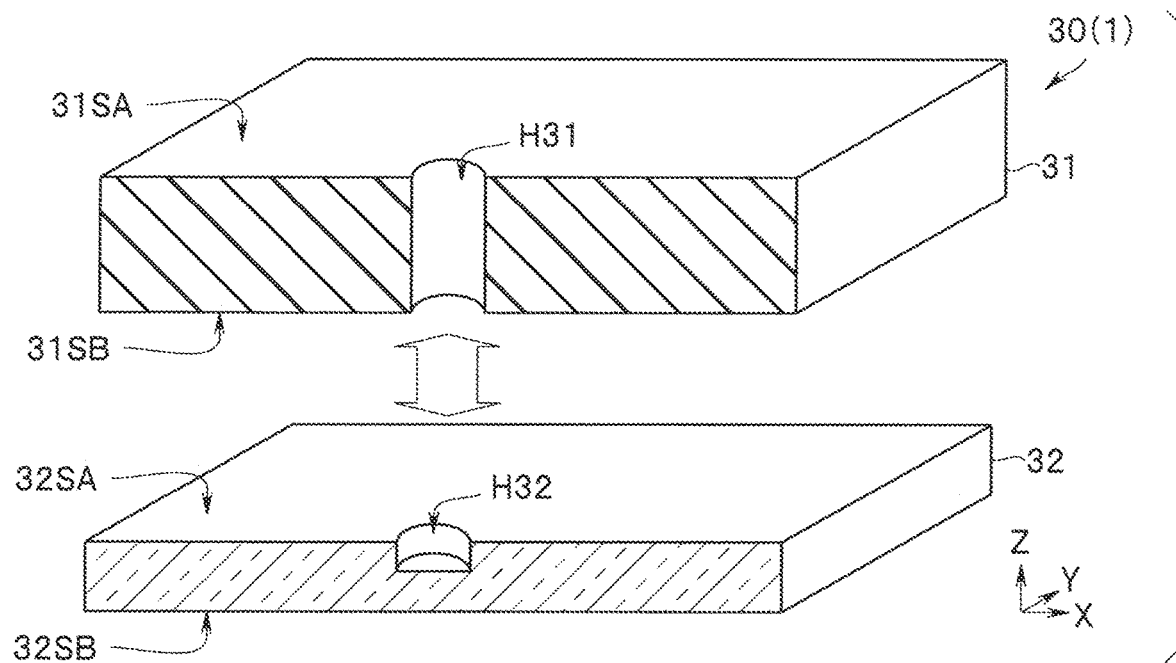
FIG. 4 is an exploded perspective cross-sectional view of a ferrule of the optical transducer of the first embodiment.

As illustrated in FIG. 4, the ferrule 30 is composed of the opaque first holding member 31 at which the through-hole H31 is formed being bonded to the transparent second holding member 32 at which the recess H32 is formed.

A plurality of ferrules can be easily manufactured by cutting a bonded substrate obtained by bonding a silicon substrate including a plurality of first holding members 31 and a glass substrate including a plurality of second holding members 32. A bonded surface of the bonded substrate is a direct bonded surface or an adhesive surface using an adhesive agent for glass (for example, glass frit).

A deep straight through-hole having a wall surface perpendicular to the principal surface and having a cross-sectional shape which does not change, is formed with high accuracy through anisotropic etching using a Deep-RIE method (Bosch method) on the silicon substrate. In the Deep-RIE method, for example, a bottom is etched while a protective layer is formed on a side wall by alternately repeating an isotropic etching process using sulfur hexafluoride and a passivation (protective layer formation) process using a fluorine resin gas. The glass substrate having the recess H32 of a depth D is, for example, manufactured using a molding method using a mold.

Note that the shapes of the through-hole H31 and the recess H32 in an optical axis orthogonal direction may be a triangle, a square or a hexagon as long as the through-hole H31 and the recess H32 can hold the optical fiber 20. For example, a size of the cross-sectional shape of the through-hole H31, which is sometimes referred to as an "inner diameter", will be referred to as an "inside dimension" in a case where the cross-sectional shape is not a circle.

Note that the inner diameter of the recess H32 may be greater than the inner diameter of the through-hole H31. In a case where the optical fiber 20 is covered with a protective tube, a ferrule in which the inner diameter of the through-hole H31 is slightly greater than an outer diameter of the protective tube, and the inner diameter of the recess H32 is smaller than the outer diameter of the protective tube and is slightly greater than an outer diameter of the optical fiber 20, may be used. Only the distal end portion of the optical fiber 20, which is not covered with the protective tube, is inserted into the recess H32.

Second Embodiment

An optical transducer and an endoscope in an embodiment and a modification which will be described below are similar to the optical transducer 1 and the endoscope 9 and provide the same effects, and thus, the same reference numerals will be assigned to components having the same functions, and description will be omitted.

Figure 5:
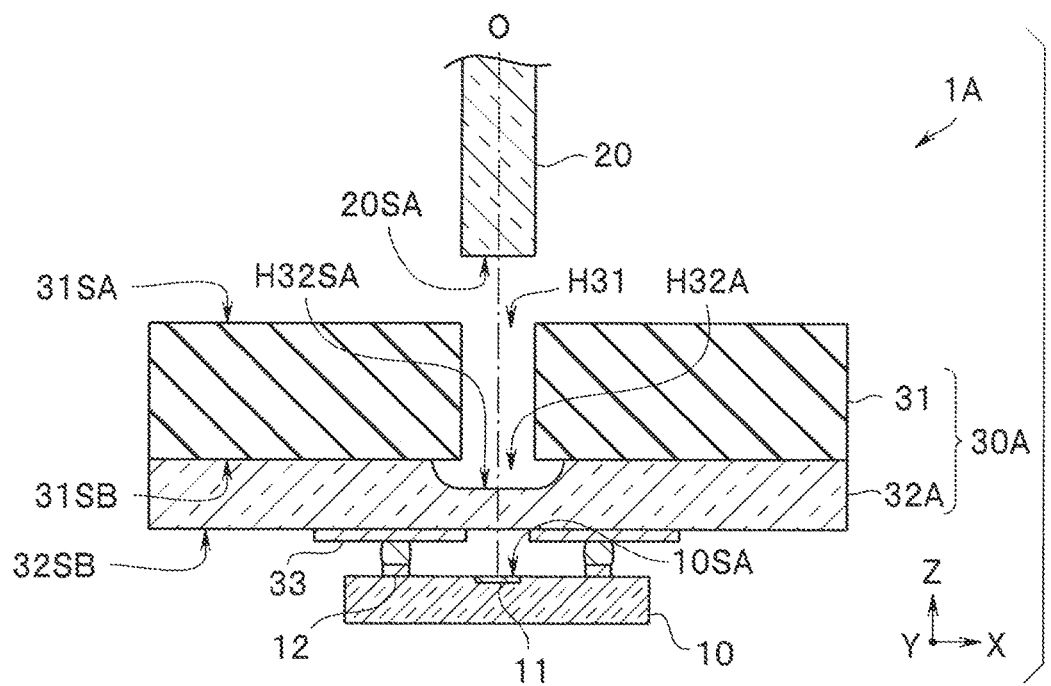
FIG. 5 is an exploded cross-sectional view of an optical transducer of a second embodiment.

In an optical transducer 1A in a second embodiment illustrated in FIG. 5, an inner diameter (inside dimension) of the cross-sectional shape orthogonal to the optical axis O, of the recess H32A of the second holding member 32A becomes smaller from the opening surface toward the bottom H32SA.

The through-hole H31 and the recess H32A of the ferrule 30A of the optical transducer 1A is formed through etching processing of a bonded substrate obtained by bonding a silicon substrate and a glass substrate. More specifically, first, the through-hole H31 is formed using an anisotropic etching process of the silicon substrate. The glass substrate becomes an etching stop layer of anisotropic etching. The through-hole H31 has a wall surface perpendicular to the principal surface, and thus, the inner diameter does not change in a depth direction and is the same.

After the anisotropic etching, the recess H32A is formed on the glass substrate using an isotropic etching process. In the isotropic etching, etching speed in a depth direction (optical axis direction) of the recess H32A is the same as etching speed in a principal surface direction (optical axis orthogonal direction), and thus, an inner diameter of a cross-section orthogonal to the optical axis O, of the recess H32A becomes smaller toward the bottom H32SA.

The ferrule 30A of the optical transducer 1A can be manufactured by performing isotropic etching after anisotropic etching, and thus, the optical transducer 1A can be manufactured more easily than the optical transducer 1.

Third Embodiment

Figure 6:
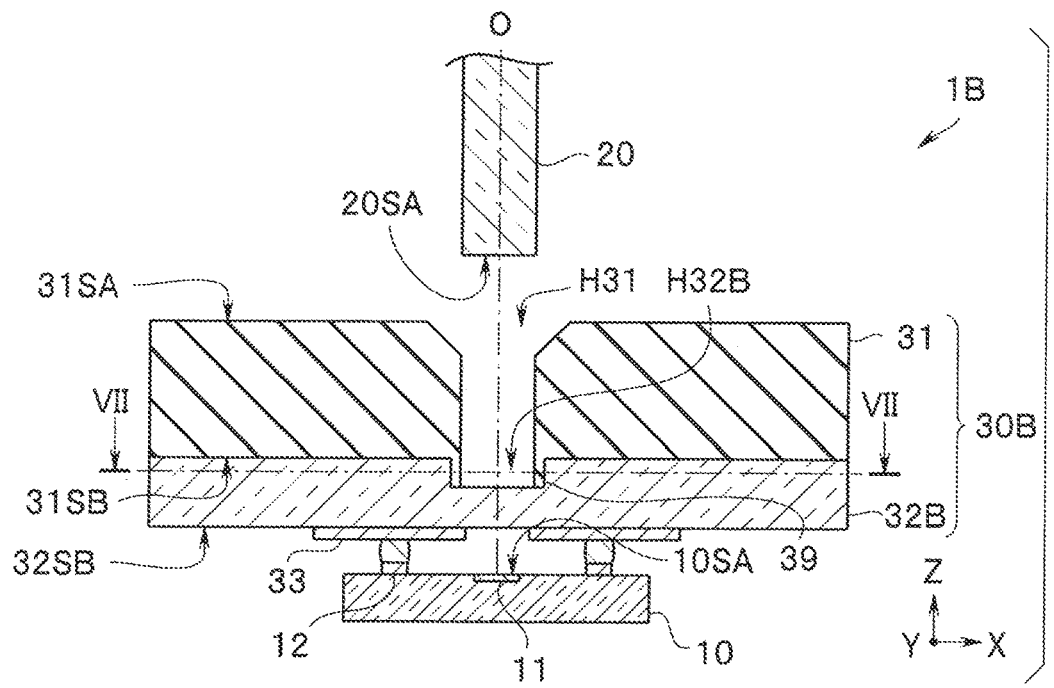
FIG. 6 is an exploded cross-sectional view of an optical transducer of a third embodiment.
Figure 7:
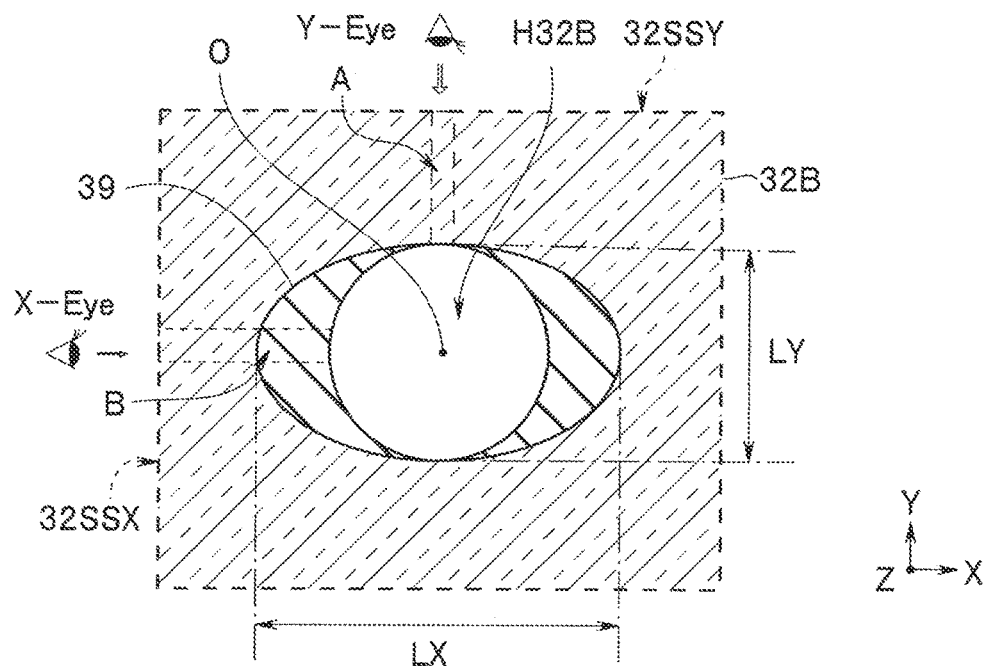
FIG. 7 is a partial cross-sectional view of the optical transducer of the third embodiment along a line VII-VII in FIG. 6.

As illustrated in FIG. 6 and FIG. 7, in an optical transducer 1B of the present embodiment, the through-hole H31 and the recess H32B have the same inner shape and the same inner diameter of cross-sections orthogonal to the optical axis O. However, part of the wall surface of the recess H32B is made of silicon 39. In other words, the wall surface of the recess H32B is silicon and glass, and a bottom of the recess H32B is glass.

In other words, the recess H32B has an inner shape of a cross-section orthogonal to the optical axis O, which is a circle having an inner diameter LY, as with the through-hole H31. However, two regions of the recess H32B, which are part of the wall surface and which face each other across the optical axis O, are not glass, but are made of silicon 39.

As illustrated in FIG. 7, the silicon 39 is also disposed inside the second holding member 32B on the cross-section orthogonal to the optical axis O and has an outer circumference in an elliptical shape. As will be described later, the recess H32B is formed by etching a central portion of a protrusion 39A (see FIG. 9) which is an elliptical cylinder using a DEEP-RIE method.

In the optical transducer 1B, space A from two side surfaces 32SSY of the second holding member 32B to the distal end of the optical fiber 20 is formed of only a transparent member including glass. Meanwhile, space B (range B) from two side surfaces 32SSX of the second holding member 32B to the distal end of the optical fiber 20 is formed of a transparent member including glass, and silicon. In other words, the optical transducer 1B includes a transparent member which fills space from part of the side surface of the second holding member 32B to the distal end of the optical fiber 20.

Thus, as illustrated in FIG. 7, the position of the distal end surface 20SA of the optical fiber 20 cannot be confirmed in a line of sight X-Eye from the side surface 32SSX. However, the position of the distal end surface 20SA of the optical fiber 20 can be confirmed in a line of sight Y-Eye from the side surface 32SSY. If the position of the distal end surface 20SA of the optical fiber 20 can be confirmed from at least one side surface, the optical fiber 20 can be reliably inserted to a predetermined position.

The through-hole H31 and the recess H32B can be successively formed in one process (DEEP-RIE etching), and thus, the optical transducer 1B can be manufactured more easily than the optical transducer 1. Further, part of the side wall of the recess H32B is silicon through which optical signals do not transmit, and thus, the optical transducer 1B leaks less light than the optical transducer 1.

Note that the opening on the first principal surface 31SA of the through-hole H31 in the optical transducer 1B has a tapered shape, and thus, the optical fiber 20 can be easily inserted. The opening of the through-hole H31 in the optical transducer 1, or the like, may also have a tapered shape.

<Manufacturing Method of Optical Transducer>

Figure 8:
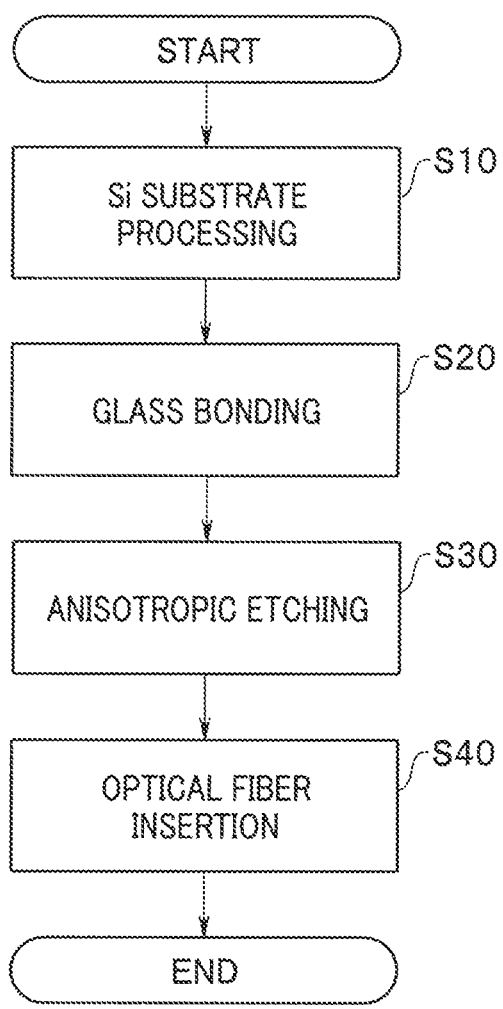
FIG. 8 is a flowchart of a manufacturing method of the optical transducer of the third embodiment.

A manufacturing method of the optical transducer 1B will be described along the flowchart in FIG. 8.

<Step S10> Silicon Substrate Processing Process

A silicon substrate 31W which includes a first principal surface 31SA and a second principal surface 31SB on an opposite side of the first principal surface 31SA and which includes a protrusion 39A on the second principal surface 31SB is manufactured.

Figure 9:
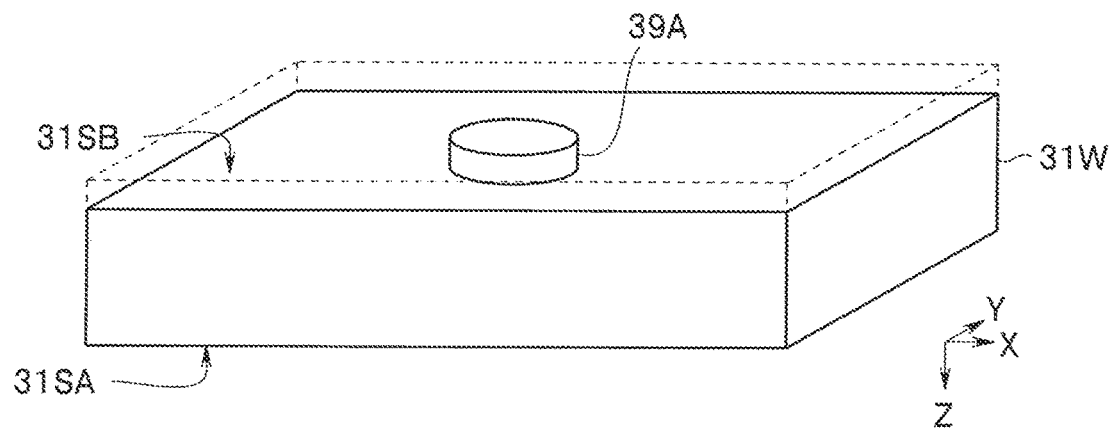
FIG. 9 is a perspective view for explaining a manufacturing method of a silicon substrate of the optical transducer of the third embodiment.

As illustrated in FIG. 9, the protrusion 39A having an upper surface which is a plane parallel to the second principal surface 31SB (the first principal surface 31SA) is manufactured by disposing a mask which covers a region which becomes the protrusion 39A on the first principal surface 31SA of the silicon substrate 31W and performing etching. As illustrated in FIG. 7, the protrusion 39A is an elliptical cylinder in which a shape of a cross-section orthogonal to the optical axis O is an ellipse having a length of a minor axis of LY and a length of a major axis of LX.

The protrusion 39A may be disposed by disposing a mask including an opening at a region which becomes the protrusion 39A on the first principal surface 31SA and disposing a silicon layer using a sputtering method or a CVD method.

<Step S20> Glass Bonding Process

Figure 10:
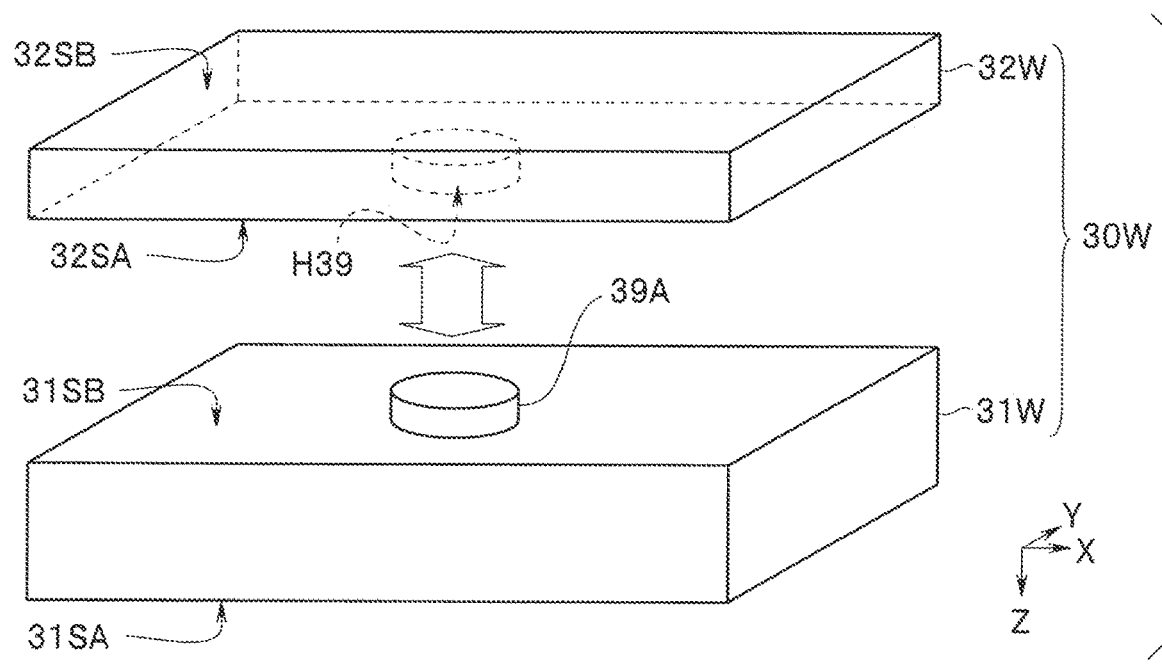
FIG. 10 is an exploded perspective view for explaining a manufacturing method of a ferrule of the optical transducer of the third embodiment.

As illustrated in FIG. 10, the protrusion 39A is embedded into a glass substrate 32W by disposing the glass substrate 32W on the second principal surface 31SB of the silicon substrate 31W.

For example, the bonded substrate 30W is manufactured by laminating the glass substrate 32W which includes the recess H39 on the third principal surface 32SA and the silicon substrate 31W which includes the protrusion 39A on the second principal surface 31SB and bonding each other through direct bonding or using an adhesive agent for glass. Note that the recess H39 is set so that the protrusion 39A is fitted.

The glass substrate 32W which includes the recess H39 on the third principal surface 32SA can be manufactured, for example, using a molding method using a mold or through processing (etching, sandblasting) of flat glass.

The glass substrate 32W can also be manufactured by pouring molten glass on the first principal surface 31SA of the silicon substrate 31W, which includes the protrusion 39A, cooling the molten glass, grinding an outer surface of the glass and processing the glass so as to have a predetermined thickness.

<Step S30> Anisotropic Etching Process

Figure 11:
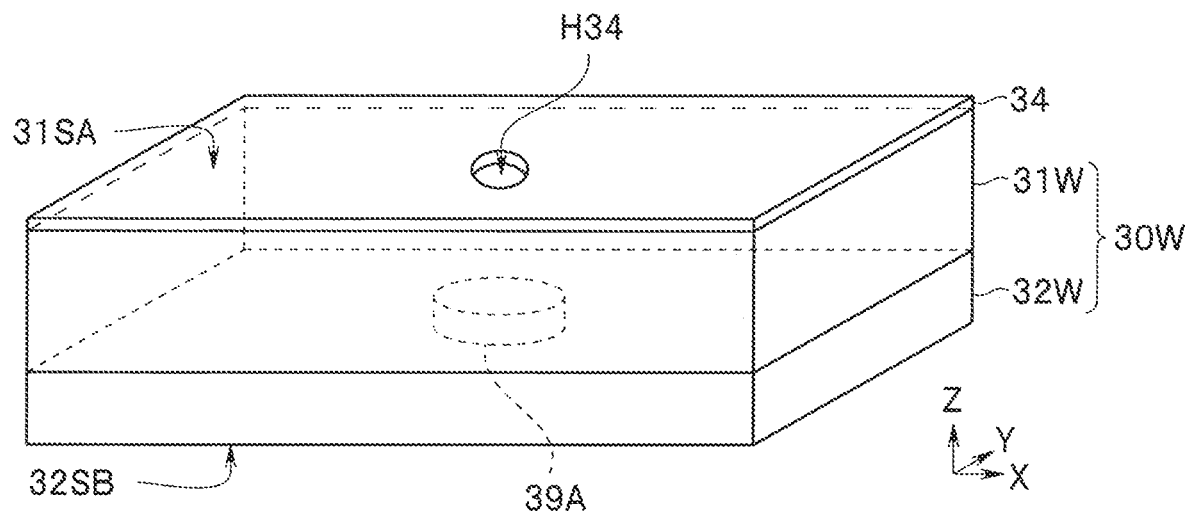
FIG. 11 is a perspective view for explaining the manufacturing method of the ferrule of the optical transducer of the third embodiment.

As illustrated in FIG. 11, an etching mask 34 which includes an opening H34 is disposed on the first principal surface 31SA of the silicon substrate 31W of the bonded substrate 30W. The circular opening H34 is disposed at a position inscribed in space located in an extension of the protrusion 39A in an optical axis direction and has a diameter which is slightly greater than the outer diameter of the optical fiber 20.

The through-hole H31 which leads to the second principal surface 31SB from the first principal surface 31SA, and the recess H32B which passes through the protrusion 39A are successively formed using the etching mask 34 using the DEEP-RIE method. The recess H32B which is formed after the through-hole H31 is formed communicates with the through-hole H31.

Figure 12:
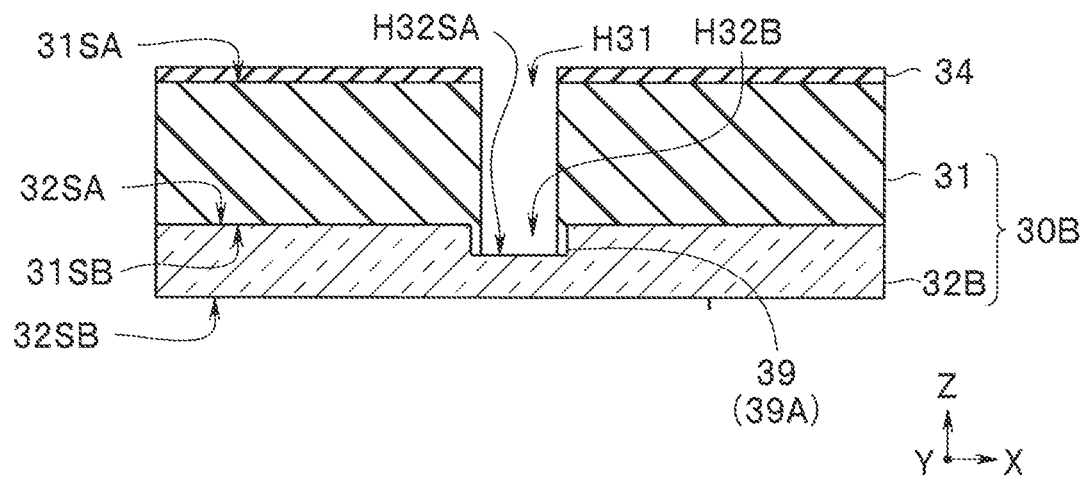
FIG. 12 is a cross-sectional view for explaining the manufacturing method of the ferrule of the optical transducer of the third embodiment.

In the DEEP-RIE method, while silicon is etched, glass (oxide silicon) is not etched. Thus, as illustrated in FIG. 12, when the recess H39 which passes through the protrusion 39A is formed, the bottom H39SA made of glass is not etched. Thus, a depth of the recess H32B is the same as a height of the protrusion 39A.

While not illustrated, a plurality of ferrules 30B are manufactured by cutting the bonded substrate 30W on which the through-holes H31 and the recesses H39B are formed.

<Step S40> Optical Fiber Insertion Process

The distal end of the optical fiber 20 is inserted into the recess H32HB through the through-hole H31.

In the optical transducer 1B, the through-hole H31 and the recess H32B can be formed in one process, and thus, the optical transducer 1B leaks less light from the side surface 32SS than the optical transducers 1 and 1A and can be easily manufactured.

Modification of Third Embodiment

Figure 13:
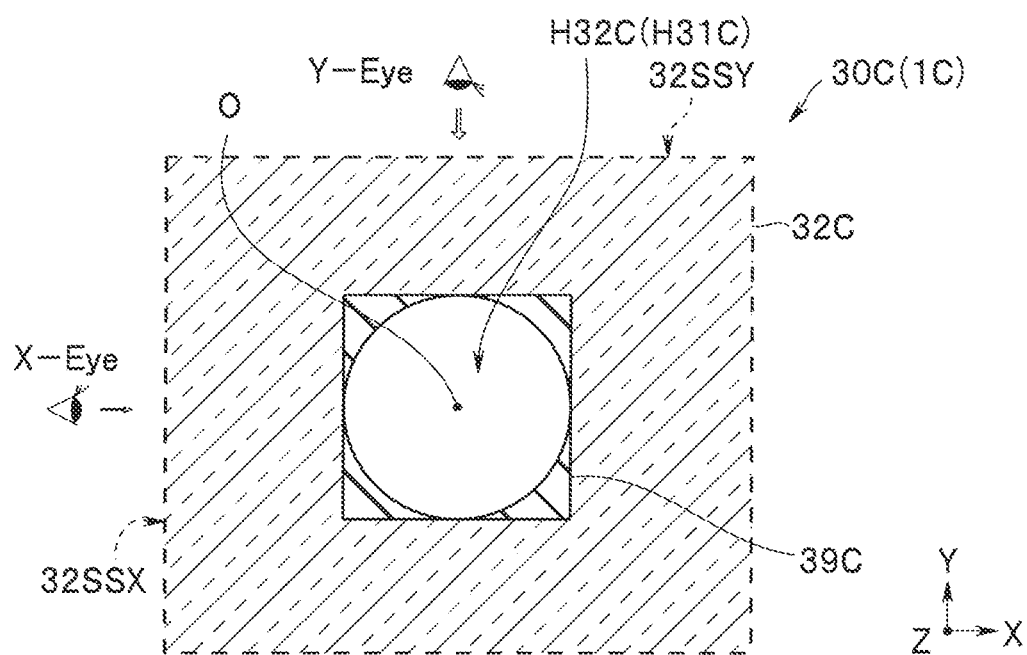
FIG. 13 is a partial cross-sectional view of a ferrule of an optical transducer of modification 1 of the third embodiment.

In an optical transducer 1C in modification 1 illustrated in FIG. 13, the silicon 39C on the wall surface of a recess H32C of a second holding member 32C of a ferrule 30C has an outer shape of a cuboid. The recess H32C and the through-hole H31 of the first holding member 31 both have a circular cross-sectional shape in an optical axis orthogonal direction. The recess H32C and the through-hole H31C are inscribed in space located in an extension of the outer shape of the silicon 39C in an optical axis direction.

In the optical transducer 1C, the position of the distal end surface 20SA of the optical fiber 20 can be confirmed in lines of sight X-Eye and Y-Eye from four side surfaces 32SS.

Figure 14:
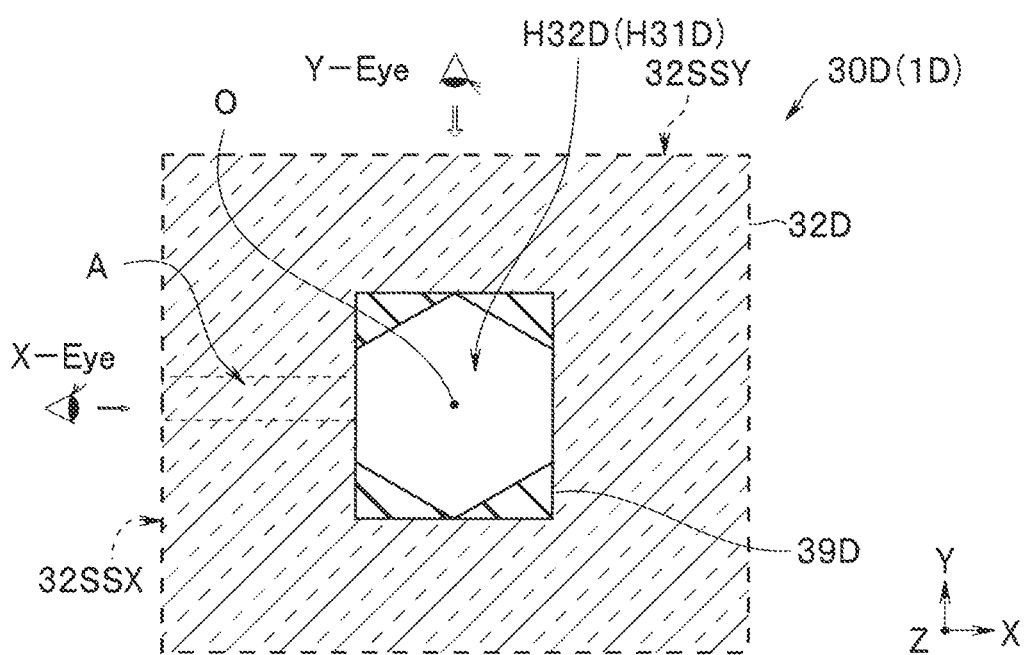
FIG. 14 is a partial cross-sectional view of a ferrule of an optical transducer of modification 2 of the third embodiment.

In an optical transducer 1D in modification 2 illustrated in FIG. 14, a through-hole H31D of a first holding member 31D and a recess H32D of a second holding member 32D of a ferrule 30D both have a cross-sectional shape in an optical axis orthogonal direction of a regular hexagon. Silicon 39D on a wall surface of the recess H32D has an outer shape of a cuboid. The recess H32D and the through-hole H31D are inscribed in space located in an extension of the outer shape of the silicon 39D in an optical axis direction.

In the optical transducer 1D, the position of the distal end surface 20SA of the optical fiber 20 can be confirmed in the line of sight X-Eye from the side surface 32SSX.

As in the modifications described above, the through-hole of the first holding member and the recess of the second holding member may have a circular inner shape or a polygonal column inner shape as long as the inserted optical fiber can be stably held. Further, the outer shape of the silicon is not limited to an elliptical cylinder unless part of the wall surface of the recess is covered with silicon.

It goes without saying that an image pickup apparatus for endoscope including the optical transducers for endoscope 1 and 1A to 1D and the image pickup device 2 of the embodiments provides effects of the optical transducers for endoscope 1 and 1A to 1D.

The present invention is not limited to the above-described respective examples, and various modifications, combinations and application are possible within a range not deviating from the gist of the invention.

What is claimed is:

1. An optical transducer for use with an endoscope, the optical transducer comprising:
   an optical device comprising:
      a light emitting surface from which an optical signal is outputted, and
      an electrode disposed on the light emitting surface; and
   a ferrule comprising:
      an opaque first holding member including a first principal surface, a second principal surface on an opposite side of the first principal surface, and a through-hole, and
      a transparent second holding member including a third principal surface and a fourth principal surface on an opposite side of the third principal surface, the third principal surface of the transparent second holding member at least indirectly abutting on the second principal surface, the electrode of the optical device being bonded to a wiring on the fourth principal surface, the third principal surface having a blind hole having a bottom surface located between the third principal surface and the fourth principal surface, the through hole and the blind hole being aligned such that a first portion of an optical fiber is disposed in the through hole and a second portion of the optical fiber, including a distal end face of the optical fiber, is disposed in the blind hole.

2. The optical transducer for endoscope according to claim 1, wherein the opaque first holding member is made of silicon, and the transparent second holding member is made of glass.

3. The optical transducer for endoscope according to claim 1, wherein the distal end face of the optical fiber is located between the bottom of the blind hole and the third principal surface.

4. The optical transducer for endoscope according to claim 1, wherein an inside dimension of the blind hole at the transparent second holding member becomes smaller toward the bottom.

5. The optical transducer for endoscope according to claim 1, wherein a first inside dimension of the through-hole at the opaque first holding member and a second inside dimension of the blind hole at the transparent second holding member have a same cross-sectional area which does not change in a direction from the first principal surface to the bottom of the blind hole.

6. The optical transducer for endoscope according to claim 1, wherein the second principal surface includes first and second protrusions extending from the second principal surface around a circumference of an opening of the through hole on the second principal surface, the first and second protrusions being separated by a first gap and a second gap at the circumference of the opening; and the first and second protrusions are disposed in the blind hole such that a first circumferential portion of the second portion of the optical fiber is exposed to the first and second protrusions of the opaque first holding member and a second circumferential portion of the second portion of the optical fiber is exposed to the transparent second holding member via the first gap and the second gap.

7. The optical transducer for endoscope according to claim 1, wherein an opening of the through hole in the first principal surface has a tapered shape.

8. The optical transducer for endoscope according to claim 1, wherein the opaque first holding member comprises at least one protrusion that protrudes into the blind hole of the transparent second holding member; and the at least one protrusion at least partially defines walls of the blind hole in the transparent second holding member, the blind hole having a same cross section as the through hole.

9. The optical transducer for endoscope according to claim 8, wherein a cross-sectional shape of an outer surface of the at least one protrusion orthogonal to an optical axis of the optical fiber is elliptical.

10. The optical transducer for endoscope according to claim 8, wherein a cross-sectional shape of an outer surface of the at least one protrusion orthogonal to an optical axis of the optical fiber is square.

11. The optical transducer for endoscope according to claim 8, wherein a cross-sectional shape of an inner surface of the at least one protrusion orthogonal to an optical axis of the optical fiber is a polygon.

12. An endoscope comprising:

an insertion portion;

an optical fiber having a first portion and a second portion including a distal end face of the optical fiber; and an optical transducer disposed at a distal end portion of the insertion portion, wherein the optical transducer comprises:

an optical device comprising:
a light emitting surface from which an optical signal is outputted, and
an electrode disposed on the light emitting surface; and a ferrule comprising:
an opaque first holding member including a first principal surface, a second principal surface on an opposite side of the first principal surface, and a through-hole, and
a transparent second holding member including a third principal surface and a fourth principal surface on an opposite side of the third principal surface, the third principal surface of the transparent second holding member at least indirectly abutting on the second principal surface, the electrode of the optical device being bonded to a wiring on the fourth principal surface, the third principal surface having a blind hole having a bottom surface located between the third principal surface and the fourth principal surface, the through hole and the blind hole being aligned such that the first portion of the optical fiber is disposed in the through hole and the second portion of the optical fiber, including the distal end face of the optical fiber, is disposed in the blind hole.

13. An optical transducer for use with an endoscope, the optical transducer comprising:

an optical device configured to generate an optical signal; and a ferrule comprising:
a first holding member made of silicon and including a first principal surface, a second principal surface facing the first principal surface, and a through-hole, and
a second holding member made of glass and including a third principal surface and a fourth principal surface facing the third principal surface, the third principal surface of the second holding member at least indirectly abutting on the second principal surface, the optical device being mounted on the fourth principal surface, the third principal surface having a hole having a stop surface located between the third principal surface and the fourth principal surface, the through hole and the hole being aligned such that a first portion of an optical fiber is disposed in the through hole and a second portion of the optical fiber, including a distal end face of the optical fiber, is disposed in the hole at the stop surface or between the third principal surface and the stop surface.

14. The endoscope according to claim 13, wherein the hole is a blind hole and the stop surface is a bottom of the blind hole.

15. An endoscope comprising:

an insertion portion;

an optical fiber having a first portion and a second portion including a distal end face of the optical fiber; and an optical transducer disposed at a distal end portion of the insertion portion, wherein the optical transducer comprises:

an optical device configured to generate an optical signal;

a ferrule comprising:
a first holding member made of silicon and including a first principal surface, a second principal surface facing the first principal surface, and a through-hole, and
a second holding member made of glass and including a third principal surface and a fourth principal surface facing the third principal surface, the third principal surface of the second holding member at least indirectly abutting on the second principal surface, the optical device being mounted on the fourth principal surface, the third principal surface having a blind hole having a bottom surface located between the third principal surface and the fourth principal surface, the through hole and the blind hole being aligned such that the first portion of the optical fiber is disposed in the through hole and the second portion of the optical fiber, including the distal end face of the optical fiber, is disposed in the blind hole.

16. The endoscope according to claim 15, wherein the distal end face of the optical fiber is located between the bottom of the blind hole and the third principal surface.

17. The endoscope according to claim 15, wherein an inside dimension of the blind hole at the transparent second holding member becomes smaller toward the bottom.

18. The endoscope according to claim 15, wherein a first inside dimension of the through hole at the opaque first holding member and a second inside dimension of the blind hole at the transparent second holding member have a same cross-sectional area which does not change in a direction from the first principal surface to the bottom of the blind hole.

19. The endoscope according to claim 15, wherein the second principal surface includes first and second protrusions extending from the second principal surface around a circumference of an opening of the through hole on the second principal surface, the first and second protrusions being separated by a first gap and a second gap at the circumference of the opening; and the first and second protrusions are disposed in the blind hole such that a first circumferential portion of the second portion of the optical fiber is exposed to the first and second protrusions of the opaque first holding member and a second circumferential portion of the second portion of the optical fiber is exposed to the transparent second holding member via the first gap and the second gap.

* * * * *